United States Patent [19]

Wozencroft

[11] Patent Number: 5,573,513
[45] Date of Patent: Nov. 12, 1996

[54] PREFILLED CARTRIDGE SYRINGE WITH NEEDLE SYSTEM

[75] Inventor: Robert M. Wozencroft, Surbiton, England

[73] Assignee: Sterimatic Holdings Limited, Tortola, Virgin Islands (Br.)

[21] Appl. No.: 356,210

[22] PCT Filed: May 26, 1993

[86] PCT No.: PCT/GB93/01087

§ 371 Date: Dec. 14, 1994

§ 102(e) Date: Dec. 14, 1994

[87] PCT Pub. No.: WO93/25254

PCT Pub. Date: Dec. 23, 1993

[30] Foreign Application Priority Data

Jun. 16, 1992 [GB] United Kingdom .................. 9212742

[51] Int. Cl.⁶ ........................................ A61M 5/32
[52] U.S. Cl. ........................ 604/198; 604/263; 128/919
[58] Field of Search ...................................... 604/110, 187, 604/188, 192, 195, 197, 198, 218, 263, 221, 222, 224, 229; 128/919

[56] References Cited

U.S. PATENT DOCUMENTS

| | | |
|---|---|---|
| 4,820,275 | 4/1989 | Haber et al. . |
| 4,946,446 | 8/1990 | Vadher . |
| 5,106,379 | 4/1992 | Leap ......................... 604/198 |
| 5,135,510 | 8/1992 | Maszkiewicz et al. ................. 604/195 |
| 5,135,514 | 8/1992 | Kimber .................... 604/240 |
| 5,169,392 | 12/1992 | Ranford et al. .......................... 604/198 |
| 5,176,656 | 1/1993 | Bayless ................................... 604/198 |
| 5,282,793 | 2/1994 | Larson ................................... 604/192 |

FOREIGN PATENT DOCUMENTS 0 268 445  5/1988  European Pat. Off. .
WO90/14112  11/1990  WIPO .

*Primary Examiner*—Corrine M. McDermott
*Assistant Examiner*—Cris L. Rodriguez
*Attorney, Agent, or Firm*—Young & Thompson

[57] ABSTRACT

A syringe system 1 for use with a prefilled injectate cartridge 9 comprises a hollow cylindrical barrel 2 having an outlet 3 at one end for passage of liquid to be expelled along a hollow pointed needle 5 by depression of a plunger 12. A protective sleeve 14 is mounted on the barrel 2 and is slidable along the barrel between a contracted position in which the needle 5 projects through an apertured end 15 of the sleeve 14, and an extended position in which the point of the needle 5 is located within the sleeve 14 to shield the point of the needle. Interengaging formations 22, 24, 26 on the barrel 2 and sleeve 14 are provided for retaining the sleeve 14 in the extended position, and a spring 19 is provided for resiliently biasing the sleeve 14 towards its extended position so that the sleeve 14 will automatically assume its extended position, and be retained therein by the interengaging formations 22, 24, 26, on release of pressure applied in the direction of contracting movement. Further interengaging formations 24, 23 are provided on the barrel 2 and sleeve 14 for retaining the sleeve in the contracted position to enable location of the needle 5 at the site of injection, the engagement of these formations being automatically released on depression of the plunger 12. Automatic shielding of the needle thereby takes place without requiring any specific operator action.

10 Claims, 4 Drawing Sheets

PREFILLED CARTRIDGE SYRINGE WITH NEEDLE SYSTEM

This invention relates to syringe systems.

After use of a syringe to perform an injection or take up a sample of blood from a patient, there is a risk that doctors or nurses will accidentally prick themselves with the needle of the syringe. This phenomenon is known as "needle stick" and can be highly dangerous due to the risk of transfer of blood-related diseases.

European Patent Specification No. 0268445 discloses a fitment for a syringe in the form of a two-part protective sleeve which surrounds the needle and which, together with the needle, is connectable to, and disconnectable from, the needle connector of the syringe barrel in place of a conventional needle. The sleeve has two sleeve parts which are movable relative to one another from a contracted position, in which the point of the needle projects from the sleeve to an extent to enable an injection to be effected, to an extended position, in which the point of the needle is located within the sleeve to shield the point of the needle. During such movement the two sleeve parts are guided relative to one another by a projection engaging in a track, and a compression spring within the sleeve ensures that the sleeve automatically assumes its extended position, and is locked in that position, after withdrawal of the needle from the patient.

Such a fitment is extremely effective in guarding against needle stick as it ensures that the point of the needle is shielded immediately after withdrawal from the patient without any need for operator action. Furthermore the fitment may be disposed of after use without any danger of the point of the needle being re-exposed. Similar advantages are obtained in use of the syringe fitments disclosed in European Patent Specification No. 0367398. However such fitments are in the form of sealed units incorporating needles, and it is not possible for conventional needles to be fitted to such units or for the units to be fitted to pre-filled syringes or pre-filled cartridge systems in which the needle is either supplied fitted to the barrel or in a common pack for fitting to the barrel. Also the sleeve is initially held in a partially contracted position in which only the tip of the needle is exposed when supplied for use, the sleeve being subsequently moved back by contact with the patient's skin as the needle is introduced into the patient, and this can render the fitment unsuitable for certain applications in which particularly accurate location of the needle at an injection site is required or in which it is necessary for injectate to first be drawn into the syringe by inserting the needle into an injectate bottle or vial.

It is an object of the invention to provide a novel form of syringe system which guards against needle stick and which is capable of being used in a number of applications for which the above-described fitment is unsuitable.

According to the present invention there is provided a syringe system as defined by the accompanying claims.

The protective sleeve of such a syringe system can be temporarily held in the retracted position by the second retaining means in order to enable accurate location of the tip of needle at an injection site or to enable introduction of the needle into an injectate bottle or vial. Since the sleeve is retained in the contracted position away from the tip of the needle during location of the needle, rather than being held in contact with the patient's skin as in the prior arrangement, sensitive control is obtained during location of the needle. Furthermore, after the point of the needle has been located in a patient's vein, the action of depressing the plunger to deliver the required dose of injectate automatically results in release of the second retaining means so as to cause the sleeve to be moved to the extended position under the action of the biasing means and to be retained by the first retaining means in the extended position in which it shields the point of the needle. Such a shielding action is automatically initiated by the action of delivering the injection dose, so that safe shielding of the needle is not dependent on specific operator action, and any risk of the needle being left accidentally exposed after use is obviated. However the needle can be re-exposed if required by taking specific manual action to release the first retaining means.

Such an automatic shielding action is advantageous in a number of fields of application, and finds particular application in a pre-filled cartridge system in which a pre-filled cartridge is introduced into the syringe barrel and is punctured by a double-ended needle through which injectate is to be delivered to the patient under the action of a plunger. In such a system the needle is integral with the syringe barrel, and it is convenient for the needle assembly to be supplied with the sleeve ready fitted to the barrel and locked in the extended position in which it surrounds the needle. This ensures that the needle is protected prior to use without having to be supplied with a removable protective sheath. Furthermore the sleeve is retained in the extended position during fitting of the cartridge to the barrel and fitting of the plunger to the cartridge, and specific operator action is required to enable the sleeve to be moved back to the contracted position to permit an injection to be performed. Such action requires previous fitting of the cartridge to the barrel, so that the needle cannot be exposed either before the cartridge has been fitted to the assembly or if the cartridge is subsequently removed after an injection has been performed.

In order that the invention may be more fully understood, syringe systems in accordance with the invention will now be described, by way of example, with reference to the accompanying drawings, in which.

Figures 1, 2, 3:
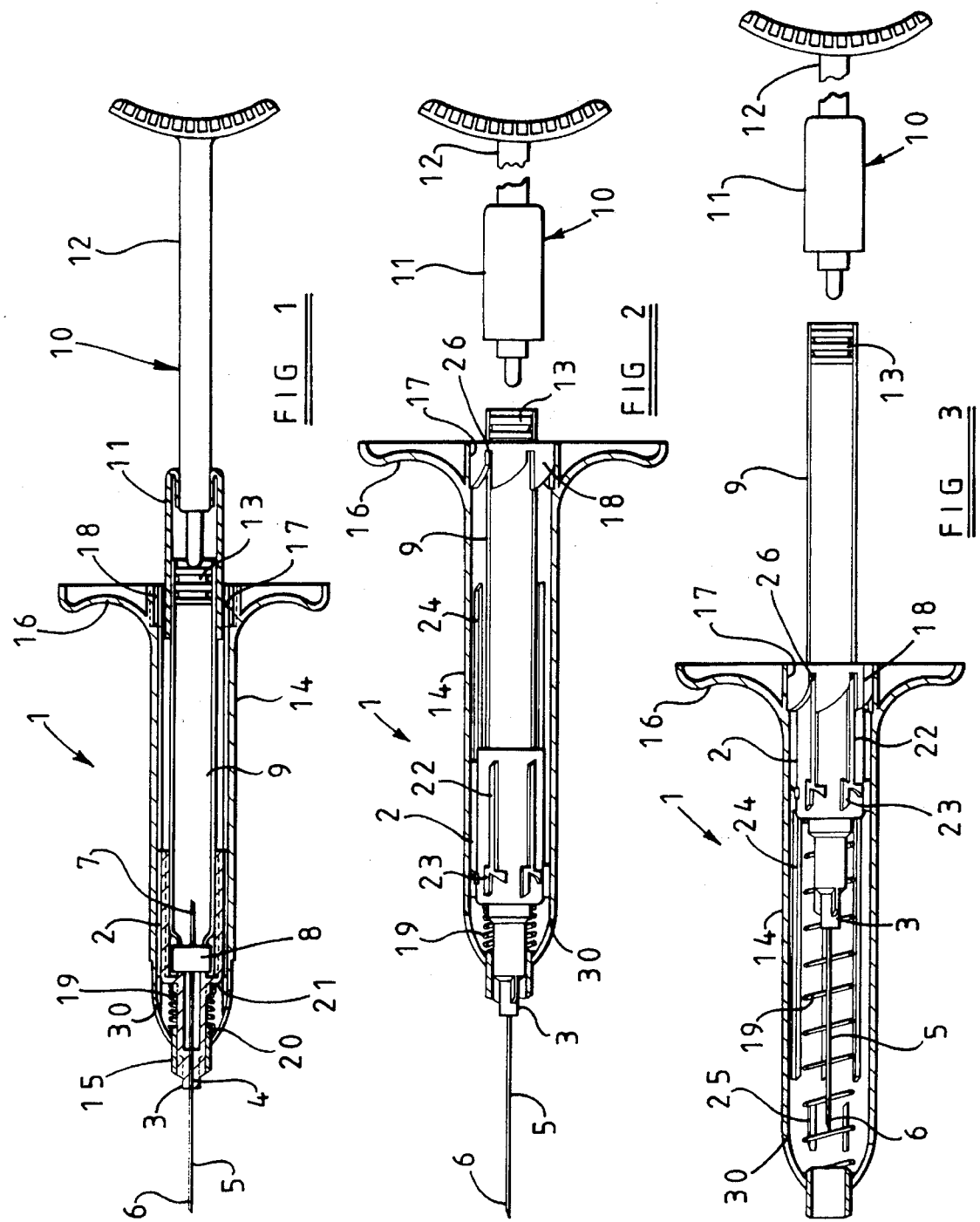
FIG. 1 is an axial section through a first syringe system.
FIGS. 2 and 3 show the first syringe system partly in axial section and partly disassembled, in two operational positions.

Referring to FIG. 1, the syringe system 1 comprises a hollow cylindrical barrel 2 made of transparent plastics material having at one end 3 an outlet 4 through which a double-ended needle 5 extends. The needle 5 has a first pointed end 6 for puncturing the patient's skin and a second pointed end 7 for puncturing a rubber membrane of an end closure 8 at one end of a glass cartridge 9 which is pre-filled with injectate. An actuator 10 comprises a collar part 11 which is a push fit over the opposite end of the cartridge 9, and a plunger 12 which is slidable within the collar 11 so as to displace a piston 13 within the glass cartridge 9 in order to expel injectate from the cartridge 9 along the needle 5 in known manner.

In addition a transparent plastics protective sleeve 14 is mounted on the barrel 2 and is slidable along the barrel 2 between a contracted position (see FIG. 2) in which the needle 5 projects from an apertured end 15 of the sleeve 14, and an extended position (see FIG. 3) in which the needle 5 is located within the sleeve 14 to shield the pointed end 6 of the needle.

The sleeve 14 is provided with an outwardly projecting flange 16 at its opposite end which is intended to be grasped during administration of an injection to the patient. Furthermore the flanged end of the sleeve 14 has an opening 17 into which an annular insert part 18 is force fitted during assembly in order to retain the barrel 2 within the sleeve 14. A compression spring 19 is located between an inner flange 20 on the sleeve 14 and a shoulder 21 on the barrel 2 in order to tend to bias the sleeve 14 towards the extended position.

As may be appreciated more readily by referring to the partially sectioned views of FIGS. 2 and 3, the outer surface of the barrel 2 is provided with a series of longitudinally extending external ribs 22. Although only two ribs 22 are visible in the figures, six such ribs 22 are in fact equiangularly spaced about the circumference of the barrel 2. Furthermore each rib 22 is provided at one end with a latch part 23. Furthermore the inner surface of the sleeve 14 is provided with first internal ribs 24 and second internal ribs 25 angularly offset from the first ribs 24.

The external ribs 22 on the barrel 2 cooperate with the internal ribs 24 and 25 on the sleeve 14 and with six retaining recesses 26 in the insert part 18 to guide the sleeve 14 on the barrel 2 and to provide the required operational action which will be described below with reference to FIGS. 4 to 12. Each of FIGS. 4 to 12 shows schematically, on the left hand side of the figure, the syringe system 1 in a particular operational state, and, on the right hand side of the figure, the positioning of the external ribs 22 on the barrel 2 in relation to the internal ribs 24 and 25 on the sleeve 14 and the recesses 26 in the insert part 18. It will be appreciated that, for convenience, the ribs 22, 24 and 25 and the recesses 26 in the insert part 18 are shown in developed view, and only some of these ribs and recesses are shown.

Figure 4:
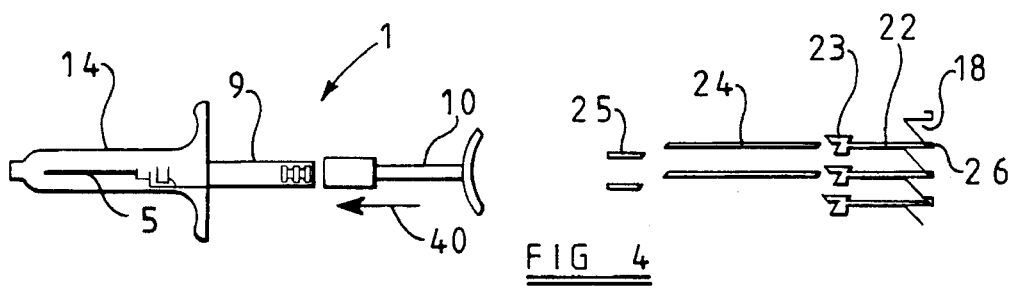
FIGS. 4 to 12 show schematic diagrams of the first syringe system in different operational positions, together with diagrams showing the relative positions of external ribs on the barrel and internal ribs on the sleeve.
Figure 5:
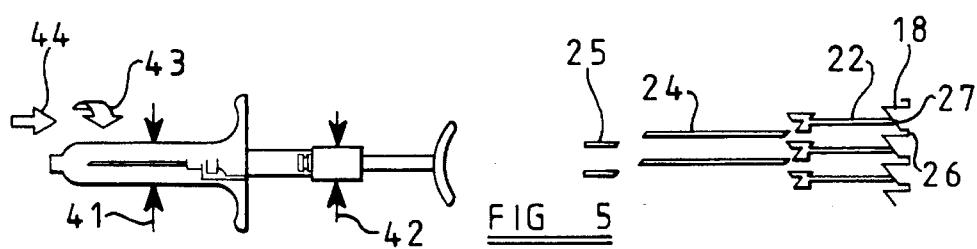

The needle assembly, that is the assembly of the barrel 2, needle 5 and sleeve 14, is initially supplied without a pre-filled cartridge 9 in position, and with the needle 5 shielded within the sleeve 14 as shown in FIG. 4. In this position (corresponding to the position shown in FIG. 3) the sleeve 14 is extended in relation to the barrel 2 so that the external ribs 22 on the barrel 2 engage within the recesses 26 in the insert part 18 and the latch parts 23 of the external ribs 22 are positioned so as to cooperate with the internal ribs 24 on the sleeve 14 to prevent the needle 5 being exposed by accidental retraction of the sleeve 14. Furthermore, since the barrel 2 is wholly contained within the sleeve 14, there is no operation which may be performed on the assembly which will result in exposure of the needle 5 by retraction of the sleeve 14. With the needle assembly in this position a cartridge 9 may be introduced into the sleeve 14 so as to cause the rubber membrane of the end closure 8 of the cartridge 9 to be pierced by the pointed end 7 of the needle 5. The actuator 10 may then be engaged with the opposite end of the cartridge 9 by movement in the direction of the arrow 40. The cartridge 9 fits tightly into both the barrel 2 and the collar part 11 of the actuator 10 in order to prevent relative rotation between these components in use.

A manual setting operation is then required in order to expose the needle 5 so as to render the syringe system ready for use in carrying out an injection. In order to perform this setting operation, the syringe system must be held in two locations, as shown by the arrows 41 and 42 in FIG. 5, using two hands, and a twisting and pushing action applied to the sleeve 14, as shown by the arrows 43 and 44 in FIG. 5. This action causes axial displacement and rotation of the insert part 18 relative to the barrel 2 so as to disengage the external ribs 22 on the barrel 2 from the recesses 26 and cause the ribs 22 to engage ramp surfaces 27 on the insert part 18, as shown on the right hand side of FIG. 5. Simultaneously the internal ribs 24 on the sleeve 14 are aligned with the gaps between the ribs 22 so as to permit retraction of the sleeve 14 relative to the barrel 2 in a subsequent operation. It is important to appreciate that this unlocking operation cannot be achieved either by means of a twisting action alone or by means of a pushing action alone applied to the sleeve 14.

Figure 6:
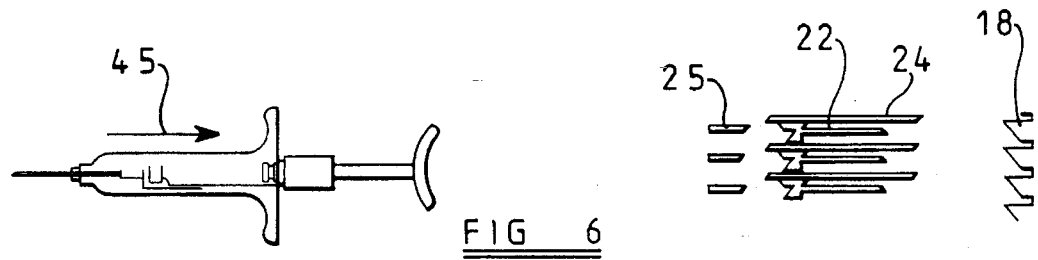

The sleeve 14 may then be retracted against the action of the compression spring 19 by pushing in the direction of the arrow 45 to expose the needle 5, as shown in FIG. 6. This causes the internal ribs 24 on the sleeve 14 to pass through the gaps between the external ribs 22 on the barrel 2, as shown on the right hand side of FIG. 6.

Figure 7:
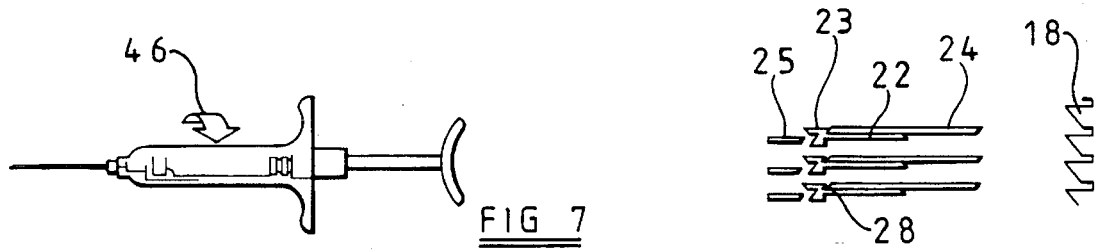

The sleeve 14 may then be temporarily locked in the retracted position, in which the needle 5 is exposed, by applying a twisting action to the sleeve 14, as shown by the arrow 46 in FIG. 7. The twisting action causes the internal ribs 24 on the sleeve 14 to be circumferentially displaced relative to the external ribs 22 on the barrel 2 so that the ribs 24 engage behind shoulders 28 on the latch parts 23 of the ribs 22 to prevent the ribs 24 moving back through the gaps between the ribs 22 under the action of the compression spring 19. This places the syringe system in the contracted position in which it is ready for use for carrying out an injection.

Figure 8:
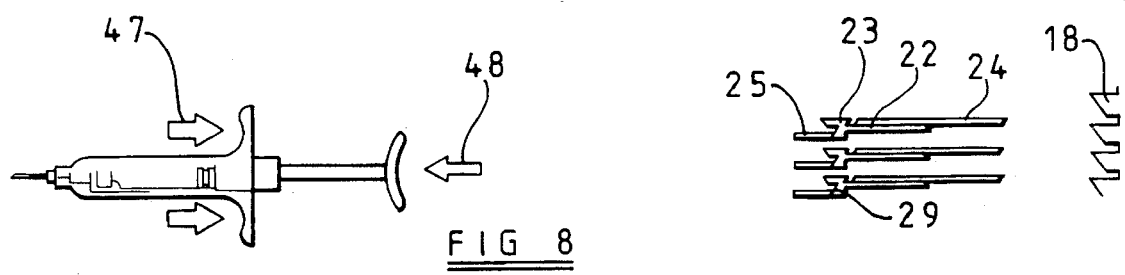

The sequence of steps for carrying out the injection are as follows. The syringe system is grasped in one hand in conventional manner with the sleeve 14 being held between the fingers in the vicinity of the flange 16 and the thumb being applied to the end of the plunger 12 of the actuator 10. The needle 5 is first caused to puncture the patient's skin until the pointed end 6 of the needle 5 is at desired location at which the injection is to be made. A squeezing action is then applied to the syringe system as shown by the arrows 47 and 48 in FIG. 8. Initially this action causes the sleeve 14 to be moved back slightly relative to the barrel 2 so that the internal ribs 25 on the sleeve 14 engage ramp surfaces 29 on the latch parts 23 of the ribs 22 the barrel 2, as shown in FIG. 8.

Figure 9:
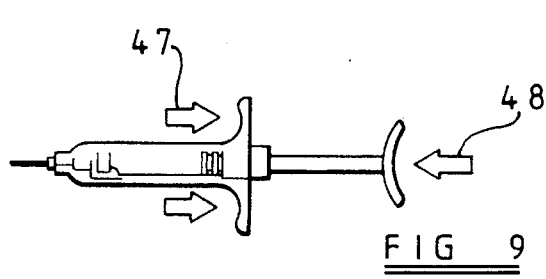
Figure 9:
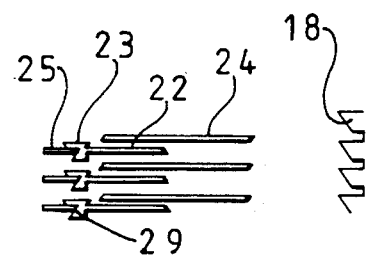

Further squeezing of the syringe system causes the ribs 25 to ride along the ramp surfaces 29 and thus results in slight relative rotation between the barrel 2 and sleeve 14 to align the ribs 24 with the gaps between the ribs 22, as shown in FIG. 9. The resulting locking engagement between the latch parts 23 and the ribs 25 prevents further retraction of the sleeve 14 relative to the barrel 2 and results in depression of the plunger 12 so as to move the piston 13 within the cartridge 9 and deliver the required dose of injectate along the needle 5.

Figure 10:
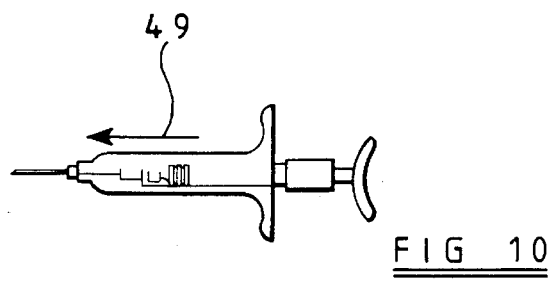
Figure 10:
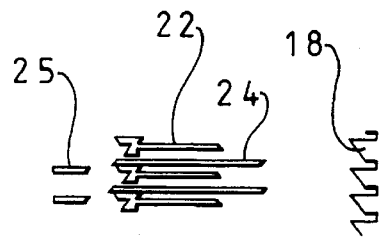
Figure 11:
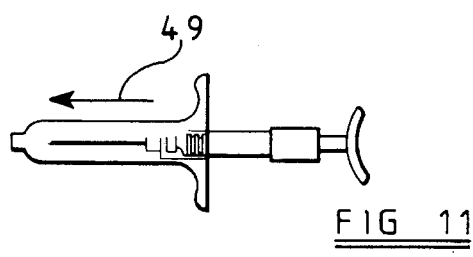
Figure 11:
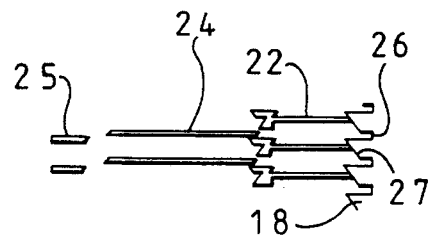

After delivery of the injectate the user's grip on the syringe system is relaxed so as to enable the sleeve 14 to move towards its extended position in the direction of the arrow 49 under the action of the compression spring 19, as shown in FIG. 10. During such movement the ribs 24 pass back through the gaps between the ribs 22. Assuming that the needle 5 has meanwhile been removed from the site of injection, the sleeve 14 moves into its extended position shielding the needle 5, as shown in FIG. 11, resulting in engagement of the ribs 22 with the ramp surfaces 27 on the insert part 18.

Figure 12:
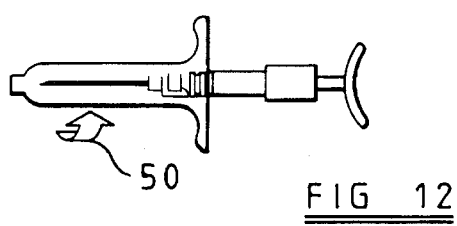
Figure 12:
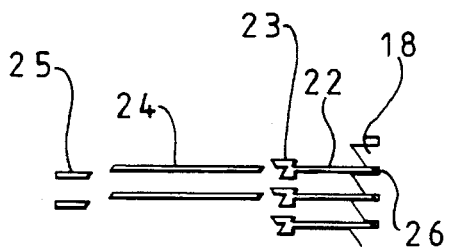

The engagement of the ribs 22 with the ramp surfaces 27 causes a slight twist to be automatically applied to the sleeve 14 as shown by the arrow 50 in FIG. 12, and this results in the ribs 22 engaging within the recesses 26 in the insert part 18 resulting in the ribs 22 assuming the same alignment relative to the ribs 24 as in the initial position shown in FIG. 4. The sleeve 14 is locked in this position by virtue of the fact that the latch parts 23 cooperate with the ribs 24 to prevent the sleeve 14 being retracted relative to the barrel 2. Thus the used syringe system (either with or without the actuator 10) can be safely disposed of without risk of accidental re-exposure of the tip of the needle.

It is to be noted that the needle 5 may be re-exposed if required, although such re-exposure can only be effected by means of the twisting and pushing action applied to the sleeve 14 as described above with reference to FIG. 5 so that there is no danger of such re-exposure being effected accidentally, and such re-exposure is prevented altogether if the cartridge 9 is removed from the needle assembly.

The particular form of the internal ribs 24 and on the sleeve 14 requires use of a two-part moulding tool for moulding of the sleeve 14, and six equiangularly distributed windows 30 are provided in the vicinity of the apertured end 15 of the sleeve 14 in order to enable fingers provided on one part of the moulding tool to form the undercuts of the ribs 25 by way of the windows 30 at the same time as the remainder of the ribs 25 are being formed by the other part of the moulding tool by way of the opening 17 of the sleeve 14.

Such a syringe system utilizing pre-filled cartridges may be used in any application in which disposable pre-filled cartridge systems are currently used. Furthermore it is envisaged that such a syringe system will replace existing reusable systems utilising pre-filled cartridges such as are used for administration of local anaesthetics in dentistry, for example.

Furthermore a broadly similar arrangement may be used in a syringe system which is supplied pre-filled with injectate during manufacture and with a needle and plunger pre-fitted thereto. In this case the syringe barrel will extend substantially the full length of the protective sleeve, and the plunger will be integrally formed with a piston within the barrel.

Furthermore a similar syringe system may be used in applications in which injectate must be drawn up into the syringe barrel by inserting the needle into an injectate bottle or vial before an injection is performed. Such an operation requires exposure of the needle by temporarily retaining the sleeve in its retracted position in order to enable the needle to be introduced into the bottle or vial. After a dose of injectate has been drawn into the syringe barrel by drawing back the plunger, the injection may be administered to the patient in a manner broadly similar to that described above with reference to FIGS. 8 to 12. A syringe system for use in such an application will now be described with reference to FIGS. 13 to 15.

Figure 13:
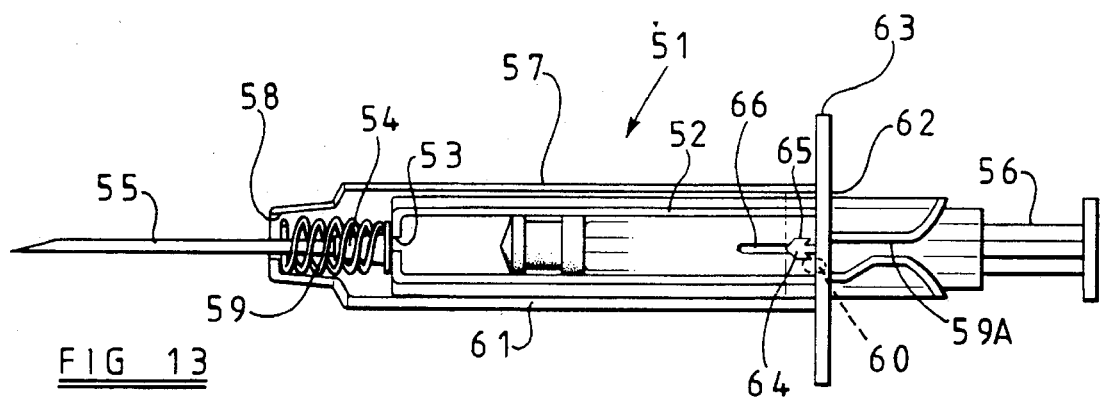
FIGS. 13 and 15 are side views of a second syringe system with the protective sleeve in two operational positions.
Figure 14:
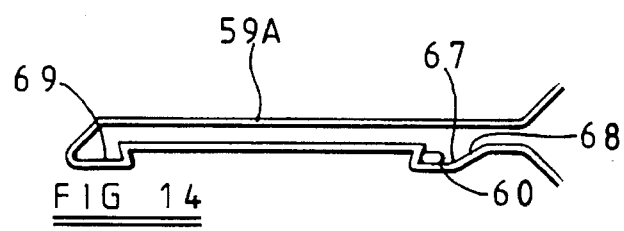
FIG. 14 is an explanatory diagram showing location of a projection within a track.
Figure 15:
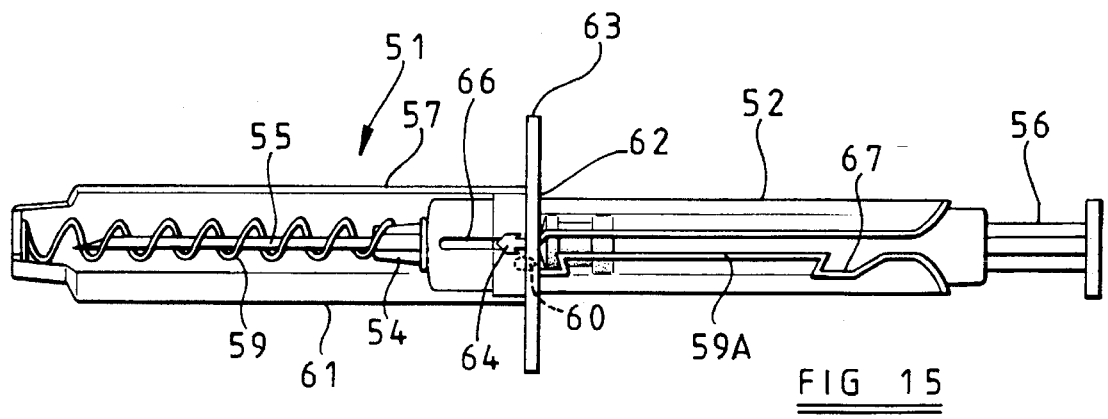
Figure 16:
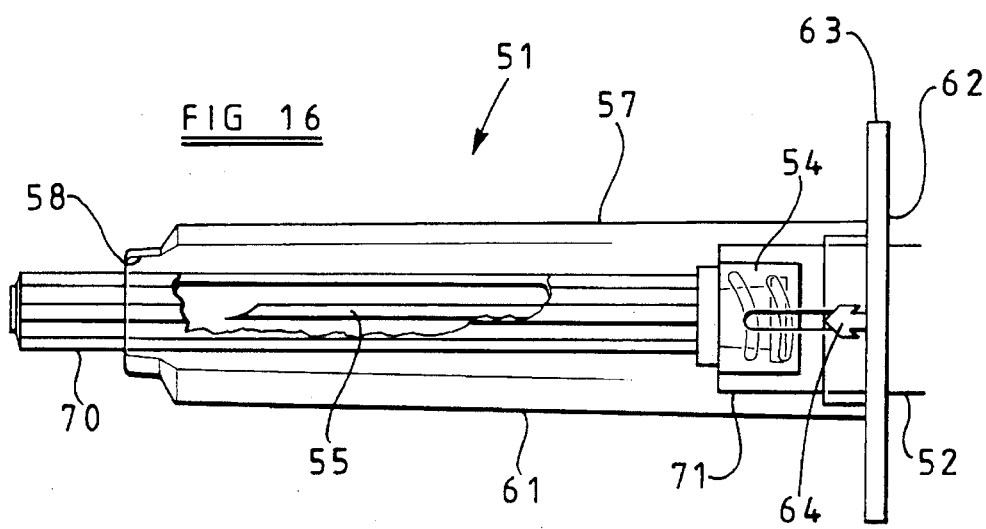
FIG. 16 is a side view of the second syringe system during removal of the needle from the syringe.

Referring to FIGS. 13 to 15, the syringe system 51 comprises a barrel 52 having at one end an outlet 53 and an integral needle connector 54 for attachment of the needle 55, and a plunger 56 displaceable within the barrel 52. A sleeve 57 is mounted on the barrel 52 and is slidable along the barrel 2 between a contracted position (see FIG. 13) and an extended position (see FIG. 15). The sleeve 57 has an opening 58 through which the needle 55 projects when the sleeve is in the contracted position. A compression spring 59 is located within the sleeve 57 between the needle connector 54 and the end of the sleeve.

As may be seen more particularly in FIG. 15, the outer surface of the barrel 52 is formed with a guide track 59A within which a projection 60 (shown in broken lines) on the inside of the sleeve 57 engages. In order to simplify assembly the sleeve 57 is formed in two parts, namely a main body part 61 of generally tubular form and an annular end part 62 having the projection 60 on its inside surface and having an outwardly projecting flange 63. During assembly, after fitting of the plunger 56 within the barrel 52 and fitting of the spring 59 within the sleeve 57, the end part 62 is slid over the barrel 52 so as to introduce the projection 60 into the track 59A from the plunger end of the barrel, and the barrel 52 is then introduced into the body part 61 until a locking arrow 64 on the end part 62 snaps into a complementary locking part 65 of a slot 66 in the wall of the body part 61. In this manner the syringe system is placed in its initial locked condition with the sleeve 57 in the extended position shown in FIG. 3.

As may be appreciated more readily by referring to the explanatory diagram of FIG. 14, the sleeve 57 is held in its initial extended position (FIG. 15) by engagement of the projection 60 within a recess 69. The syringe is set to enable a dose to be taken up from an injectate bottle by applying a twisting motion to the sleeve 57 so as to bring the projection 60 out of the recess 69 and so as to permit the sleeve 57 to be manually drawn back to the contracted position with the projection 60 moving along the track 59A. The sleeve 57 is temporarily locked in its contracted position (FIG. 13) by applying a twisting motion to the sleeve 57 to cause the projection 60 to engage within the recess 67, as shown in FIG. 14. The needle 55 is then caused to pierce the cap of the injectate bottle and the injectate drawn up by pulling back the plunger 56. Subsequently the needle 55 is withdrawn from the bottle, this action optionally resulting in the projection 60 moving out of the recess 67 so that the spring 59 moves the sleeve 57 into its extended position (FIG. 15) shielding the point of the needle 55 in which it is locked by the projection 60 engaging within the recess 69.

If required the needle used for filling the syringe may be re-sheathed and replaced by another needle for performing the actual injection. Subsequently, after removal of the protective sheath from the new needle, air is expelled from the syringe in conventional manner, and, if necessary, the syringe is re-set by applying a twisting motion to the sleeve 57 and drawing the sleeve back to the contracted position (FIG. 13). After location of the needle 55 at the intended site of injection, the dose may be administered by squeezing the syringe to depress the plunger 56. Initial depression of the plunger 56 causes the barrel 52 to be forced inwardly against the action of the spring 59 and results in the projection 60 engaging the ramp surface 68 so as to be forced out of the recess 67. Thus, on completion of the injection, as the needle 55 is removed from the patient, the projection 60 moves along the track 59A as the sleeve resumes its extended position shielding the needle in which it is locked by engagement of the projection 60 within the recess 69.

Provided that the needle 55 is detachable from the needle connector 54, such a syringe system can be used with conventional needles. Furthermore a needle may be connected to or disconnected from the needle connector 54 whilst the sleeve 57 is in its extended position shielding the point of the needle, so as to avoid any danger of needle stick during such an operation.

Re-sheathing of the needle 55 is performed by inserting a protective sheath 70 into the sleeve 57 through the opening 58 at the end of the sleeve, as shown in FIG. 8. The sheath 70 is pushed over the needle hub so that internal ribs on the sheath 70 engage the outside of the needle hub. When a sheathed needle is to be connected to the needle connector 54, the sheathed needle is inserted into the sleeve 57 through the opening 58 and the hub of the needle is screwed onto the needle connector 54 by rotating the projecting end of the sheath 70, the sheath 70 subsequently being withdrawn leaving the needle in position and shielded by the sleeve 57. Generally the needle connector 54 is a luer lock connector incorporating a tapered inner part over which the hub of the needle seats and an outer collar 71 having internal threads or projections for engaging complementary formations on the outside of the needle hub.

In order to remove the needle from the needle connector 54, an empty sheath is introduced into the sleeve 57 and engaged with the needle hub prior to unscrewing the needle from the needle connector 54 and drawing the needle within the sheath 70 out of the sleeve.

I claim:

1. A syringe system comprising an elongated hollow cylindrical barrel (2) having an outlet (3) at one end of the barrel, a hollow pointed needle (5) connected to said one end of the barrel in fluid communication with the outlet, a plunger (12) within the barrel which is axially movable by manual depression of the plunger from an outer extreme position outside the barrel to an inner extreme position within the barrel to expel liquid through the outlet (3) and along the needle (5), a protective sleeve (4) having an apertured end (15) and mounted on the barrel (2) so as to be slidable along the barrel between a contracted position in which the needle (5) projects through the apertured end (15) of the sleeve (14) to enable skin puncturing to be effected and an extended position in which the needle (5) is located within the sleeve (14) to shield the point of the needle, first retaining means (22, 24, 26) on the barrel and the sleeve operable to retain the sleeve (14) in the extended position to shield the point of the needle (5), biasing means (19) mounted on the barrel and resiliently biasing the sleeve (14) towards its extended position whereby the sleeve (14) automatically assumes its extended position, and is retained therein by the first retaining means (22, 24, 26), on release of pressure applied in the direction of contracting movement, and second retaining means (23, 24) on the barrel and the sleeve operable to retain the sleeve (14) in the contracted position and to be automatically released by the beginning of depression of the plunger (12) out of said outer extreme position to a position short of said inner extreme position.

2. A system according to claim 1, wherein the second retaining means comprises a latch formation (23) on the barrel (2) and a projection (24) on the sleeve (14) which is engageable behind the latch formation (23) on the barrel (2) by relative twisting movement manually applied between the sleeve (14) and the barrel (2) in order to retain the sleeve (14) in the contracted position.

3. A system according to claim 2, wherein one of the latch formation (23) on the barrel (2) and the projection (24) on the sleeve (14) has a ramp surface (29) which is engageable by the other of the latch formation on the barrel (23) and the projection on the sleeve (24) upon depression of the plunger (12) to expel liquid along the needle (5) in order to apply a relative twisting movement between the sleeve (14) and the barrel (2) to thereby release the second retaining means.

4. A system according to claim 1, wherein the first retaining means comprises first and second formations (24, 26) on the sleeve (14) and a projection (22) on the barrel (2) which is engageable between the first and second formations (24, 26) on the sleeve (14) by means of a relative twisting movement between the sleeve (14) and the barrel (2) imparted by the biasing means (19) as the sleeve (14) moves towards its extended position.

5. A system according to claim 1, wherein the second retaining means comprises formations (23, 24) formed by external ribs (22) on the barrel (2) and internal ribs (24, 25) on the sleeve (14) which cooperate to guide the sleeve (14) relative to the barrel (2) during sliding of the sleeve along the barrel.

6. A system according to claim 1, wherein the sleeve (14) comprises a tubular body part within having an opening (17) in the end of the body part opposite to the apertured end (15), the barrel (2) being inserted in said opening (17) during assembly, and an annular end part (18) which is formed separately from the body part and which is connected to said opposite end of the body part on assembly in order to retain the barrel (2) within the sleeve (14).

7. A system according to claim 6, wherein the first retaining means (22, 24, 26) includes a recess (26) in the annular end part (18) which is located within the opening (17) in the body part.

8. A system according to claim 1, wherein the sleeve (14) is provided with an outwardly projecting flange (16) at the opposite end of the sleeve to the apertured end (15) so that the plunger (12) is movable to expel liquid along the needle by depressing the plunger with the thumb of one hand whilst grasping the flange with the fingers of the same hand.

9. A system according to claim 1, which incorporates a pre-filled cartridge (9), wherein the barrel (2) receives one end of the cartridge (9) therein in fluid communication with the outlet (3) whereby liquid is supplied from the cartridge (9) to the needle (5) on depression of the plunger (12), and wherein the other end of the cartridge (9) projects from the opposite end of the sleeve (14) to the apertured end (15) and is connected to the plunger (12).

10. A system according to claim 1, wherein said one end of the barrel (52) incorporates a needle connector (54) detachably connecting the needle (55) to said one end of the barrel, and the sleeve (57) has an opening (58) at its end through which the needle projects when the sleeve is in its contracted position, a needle sheath (70) for covering the needle, the opening (58) being of such a size as to enable said needle sheath (70) to be passed through the opening and over the needle when the point of the needle is located within the sleeve in the extended position of the sleeve for the purpose of attaching the needle to or detaching the needle from the needle connector (54).

* * * * *